US008671551B2

(12) United States Patent
Yost et al.

(10) Patent No.: US 8,671,551 B2
(45) Date of Patent: Mar. 18, 2014

(54) PROCESS FOR NONDESTRUCTIVE EVALUATION OF THE QUALITY OF A CRIMPED WIRE CONNECTOR

(75) Inventors: William T. Yost, Newport News, VA (US); Karl E. Cramer, Yorktown, VA (US); Daniel F. Perey, Yorktown, VA (US); Keith A. Williams, West Lafayette, IN (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 13/363,413

(22) Filed: Feb. 1, 2012

(65) Prior Publication Data

US 2012/0192407 A1 Aug. 2, 2012

Related U.S. Application Data

(60) Provisional application No. 61/438,386, filed on Feb. 1, 2011.

(51) Int. Cl.
*G01R 31/28* (2006.01)
(52) U.S. Cl.
USPC .............. 29/593; 29/407.05; 29/705; 29/861; 324/537; 324/538
(58) Field of Classification Search
USPC ........ 29/593, 407.05, 705, 861; 324/537, 538
See application file for complete search history.

(56) References Cited

U.S. PATENT DOCUMENTS

| | | | |
|---|---|---|---|
| 3,157,075 A | 11/1964 | Filia et al. | |
| 3,292,413 A | 12/1966 | Falcioni | |
| 4,062,227 A | 12/1977 | Heyman | |
| 4,373,394 A * | 2/1983 | Renzel et al. | 73/606 |
| 4,385,515 A | 5/1983 | Link et al. | |
| 5,046,241 A | 9/1991 | Ricard | |
| 5,092,026 A | 3/1992 | Klemmer et al. | |
| 5,197,186 A | 3/1993 | Strong et al. | |
| 5,297,435 A | 3/1994 | Papazian | |

(Continued)

OTHER PUBLICATIONS

Cheng-Hsun, et al., "Ultrasonic Evaluation of Temper-Embrittlement for Martensitic Stainless Steel," Jun. 20, 2003, pp. 2363-2368, vol. 44, No. 11.

(Continued)

*Primary Examiner* — Peter DungBa Vo
*Assistant Examiner* — Jeffrey T Carley
(74) *Attorney, Agent, or Firm* — Andrea Z. Warmbier; Robin W. Edwards

(57) ABSTRACT

A process and apparatus for collecting data for nondestructive evaluation of the quality of a crimped wire connector are provided. The process involves providing a crimping tool having an anvil and opposing jaw for crimping a terminal onto a stranded wire, moving the jaw relative to the anvil to close the distance between the jaw and the anvil and thereby compress the terminal against the wire, while transmitting ultrasonic waves that are propagated through the terminal-wire combination and received at a receiving ultrasonic transducer as the jaw is moved relative to the anvil, and detecting and recording the position of the jaw relative to the anvil as a function of time and detecting and recording the amplitude of the ultrasonic wave that is received at the receiving ultrasonic transducer as a function of time as the jaw is moved relative to the anvil.

10 Claims, 6 Drawing Sheets

(56) References Cited

U.S. PATENT DOCUMENTS

| | | |
|---|---|---|
| 5,814,728 A | 9/1998 | Okawa et al. |
| 6,196,062 B1 | 3/2001 | Wright et al. |
| 6,393,924 B1 | 5/2002 | Eder et al. |
| 6,418,769 B1 | 7/2002 | Schreiner |
| 6,553,803 B1 | 4/2003 | Heingartner et al. |
| 7,181,942 B2 * | 2/2007 | Yost et al. ............. 72/17.2 |
| 2004/0027578 A1 * | 2/2004 | Drake et al. ............. 356/502 |
| 2004/0055354 A1 * | 3/2004 | Anton ............. 72/372 |
| 2005/0193792 A1 | 9/2005 | Yost et al. |
| 2008/0276678 A1 * | 11/2008 | Pacaud et al. ............. 72/21.4 |
| 2009/0314087 A1 * | 12/2009 | Ales et al. ............. 73/597 |

OTHER PUBLICATIONS

PCT International Search Report, PCT/US2012/023423, May 16, 2012.

* cited by examiner

PROCESS FOR NONDESTRUCTIVE EVALUATION OF THE QUALITY OF A CRIMPED WIRE CONNECTOR

CROSS-REFERENCE TO RELATED PATENT APPLICATION

This patent application claims is a nonprovisional of and claims priority to U.S. Provisional Patent Application Ser. No. 61/438,386, filed Feb. 1, 2011, the contents of which are hereby incorporated by reference in their entirety.

STATEMENT REGARDING FEDERALLY SPONSORED RESEARCH OR DEVELOPMENT

The invention described herein was made in part by employees of the United States Government and may be manufactured and used by or for the Government of the United States of America for governmental purposes without the payment of any royalties thereon or therefor.

FIELD OF THE INVENTION

This invention relates to nondestructive evaluation of the quality of a crimped connector, and more particularly to evaluation that occurs simultaneously or contemporaneously during formation of the crimped connector.

BACKGROUND OF THE INVENTION

Electrically conductive stranded wires are frequently terminated with a crimped connection as an alternative to electrical connectors made using soldering, welding, conductive adhesives, and various types of solderless techniques such as insulation displacement, compression, wire clamping and interference fit connections. Crimp connectors are often preferred because they are reliable and inexpensive, easily replaced if damaged, and can provide uniform and reproducible electrical and mechanical characteristics. However, damage to the electrically conductive wires can occur in the immediate vicinity of a crimped connection. This can cause a failure mode that significantly shortens the service life of a crimp connection leading to a failure of a system or vehicle employing the connection. Consequently, it is desirable to reliably and inexpensively evaluate the integrity of a crimped connector.

Another commonly employed technique for determining whether damage has occurred during fabrication of a crimped connector is visual inspection. Unfortunately, visual inspection is not easily employed for small wire diameters or when the crimp connection is not easily accessible, such as when the crimp connector is under a terminal apron or at a junction between a wire and its insulation.

In the installation of a crimped connector, a wire to be terminated is inserted into a terminal sized for the wire gauge that is involved. A tool designed to compress, indent and permanently deform a terminal wall around the wire to form a secure and electrically reliable connection of low resistance is used. At the microscopic level of this junction, asperities of the terminal surface contact the surface of the wire strands, while asperities of the wire strands make contact with the terminal wall. The deformation process keeps a residual stress on the junction to assure that intimate contact between the surfaces is maintained.

In the case of assembly lines where wiring harnesses are manufactured, the equipment is designed for rapid crimp formation. In wiring harness fabrication processes, many connections are made to smaller wire gauges. This requires the use of smaller diameter terminals which must be fabricated with tighter tolerances. The jaws used in the crimped tools are also smaller and are held to tighter tolerances. Therefore, crimping apparatus wear is more problematic and can more quickly and easily lead to degradation in crimp quality. Unfortunately, simple conductivity testing is not a reliable indicator of such degradation and such wear results in a crimp having a greater probability of premature malfunction.

SUMMARY OF THE INVENTION

Embodiments of the invention encompass processes for nondestructive evaluation of the quality of a crimped wire connector by using concurrently measured positional information about jaw-to-anvil distance and transformations in the characteristics of an ultrasonic transmission through the crimped connector. More specifically, these processes involve providing a crimp tool having an anvil on which a wire circumscribed by a terminal is positioned, and an upper jaw is movable relative to the anvil to compress the terminal between the anvil and the jaw, a transmitting ultrasonic transducer mounted on one of the anvil and the jaw and a receiving ultrasonic transducer mounted on the other of the anvil and jaw; moving the jaw relative to the anvil to cause crimping of the terminal against the wire; transmitting ultrasonic waves from the transmitting transducer through the crimped connector; receiving the ultrasonic wave at the receiving transducer; concurrently detecting and recording the position of the jaw and the amplitude of the ultrasonic wave as the terminal is being crimped; and predicting the quality of the crimped wire connector based on a comparison of the recorded positions and amplitudes to those of wire connectors having a known quality characteristic.

In other embodiments of the invention, an apparatus is provided for nondestructive evaluation of the quality of the crimped wire connector. This apparatus comprises a crimp tool having an anvil on which a multiple strand wire circumscribed by a terminal may be positioned, an upper jaw movable relative to the anvil to compress the terminal between the anvil and the jaw, an ultrasonic transducer mounted on one of the anvil and the jaw, and a receiving ultrasonic transducer mounted on the other of the anvil and jaw. A recordation device is provided for detecting and recording both the position of the jaw relative to the anvil and the amplitude of the ultrasonic wave that is received at the receiving transducer as a function of time. In accordance with an embodiment of this invention, tool position and ultrasonic transmission across the crimp are used for nondestructive evaluation of crimp quality and for predicting useful service life.

With an embodiment of the invention, an apparatus is provided for responding to and using rapid crimp formation in automated systems of the type frequently used to increase productivity on assembly line applications for wiring harnesses.

An approach used in certain embodiments of the invention involves establishing a relationship between the ultrasonic transmission through a wire-terminal interconnection region and the jaw-anvil closure.

DETAILED DESCRIPTION OF THE INVENTION

Figure 1:
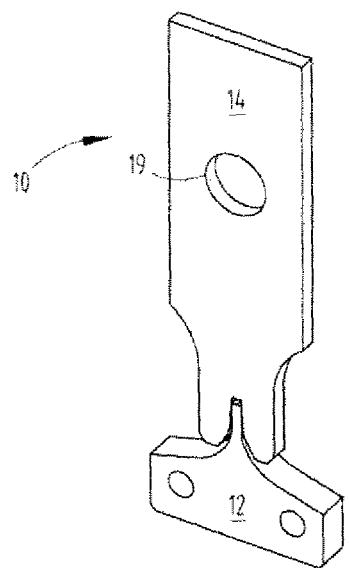
FIG. 1 is a perspective view of primary elements (jaw and anvil) of a crimp tool that may be used and/or modified for use in the practice of this invention.

Referring now to the drawings in detail, wherein like numerals indicate like elements throughout the drawings, FIG. 1 shows a crimp tool suitable for use with the invention. Crimp tool 10 includes an anvil 12 and a jaw 14 that are movable with respect to one another and which are compressed together to crimp a terminal against a wire in order to establish a crimped electrical connector. Typically, the anvil 12 remains stationary and the jaw 14 is moved relative to the anvil 12 to crimp the terminal. Anvil 12 and jaw 14 are typically fabricated from high-strength materials such as steel alloys, or any material known in the art to transmit an ultrasonic wave. The wire may comprise any wire known in the art for crimping, including but not limited to, braided wire, unbraided wire, twisted wire, stranded wire, solid wire, etc. Although the crimp tool 10 shown in FIG. 1 is configured to create a B-crimp, this is only an exemplary embodiment, and it is contemplated that the present invention applies to various types of crimp tools that create various types of crimps (e.g. F-crimp, O-crimp, C-crimp, tab-lok, W-crimp, wrap-over crimp, etc.). FIG. 1 also discloses an anchor opening 19, which is the location where the jaw 14 may be anchored to the press (not shown).

Figure 2:
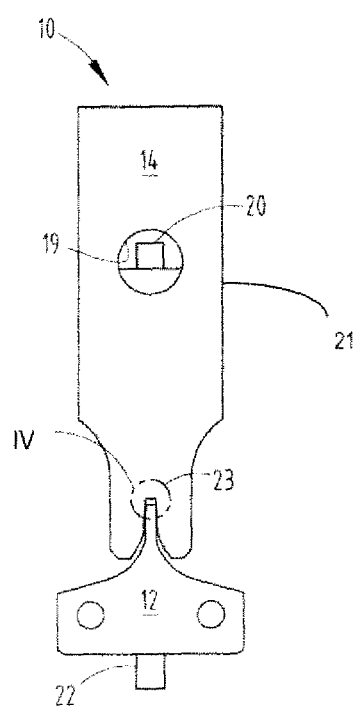
FIG. 2 is an elevational front view of a crimp tool showing possible locations of ultrasonic transducers.

As shown in FIG. 2, a transmitting ultrasonic transducer 20 is mounted on jaw 14, and a receiving ultrasonic transducer 22 is mounted on anvil 12. Although in the illustrated embodiment, the transmitting ultrasonic transducer 20 is mounted on the jaw 14 and the receiving ultrasonic transducer 22 is mounted on the anvil 12, it should be appreciated that suitable alternative embodiments of the invention may employ a transmitting ultrasonic transducer mounted on the anvil and a receiving ultrasonic transducer mounted on the jaw. It is desirable that the transducers 20 and 22 are positioned on the jaw and anvil such that an ultrasonic wave is propagated from the transmitting transducer through a meshing region 23 where a terminal is crimped onto a wire before being received at receiving transducer 22. It is desirable that the transducers 20 and 22, and the meshing region 23 where crimping occurs are axially aligned transverse to a length direction of the wire.

Figure 3:
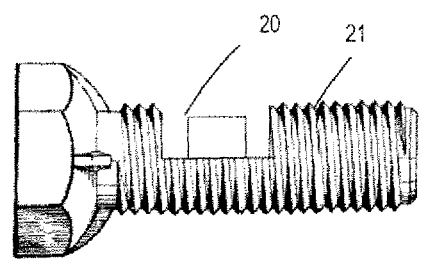
FIG. 3 is an enlarged front view of a bolt with an ultrasonic transducer mounted thereon.

In one embodiment, and as is shown in FIG. 2, the transducer 20 may be mounted to the jaw 14 via a bolt 21. The bolt 21 is typically used to secure the jaw 14 to the press (not shown) through anchor opening 19. A segment of the bolt 21 may be removed and the transducer 20 affixed to the bolt 21 with a coupling material such as an adhesive as shown in FIG. 3. Removal of the segment of the bolt 21 ensures that the bolt 21 continues to fit through the anchor opening 19 while also serving as a location to place the transducer 20. By utilizing the existing anchor opening 19 as a location to affix the transducer 20 to the jaw 14, one benefit of the present invention is that it can be retrofitted to pre-existing crimp tools.

Figure 4:
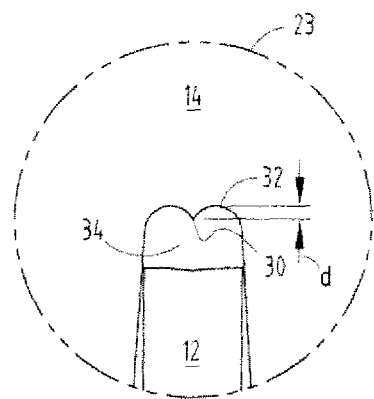
FIG. 4 is an enlarged view of the crimp zone formed between the anvil and the jaw from FIG. 2.

FIG. 4 shows an enlarged sectional view of the meshing region 23 where crimping of the terminal against a wire occurs. While not critical, in one embodiment, the distance d (the vertical displacement between a nib 30 of jaw 14 and an apex 32 of crimp region 34) may be about 0.18 mm.

Figure 5:
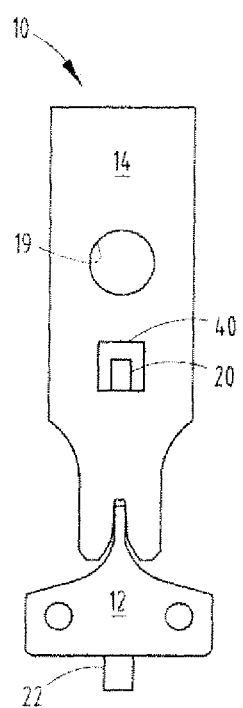
FIG. 5 is a front elevational view of an embodiment showing an alternate transducer mounting by using an opening in the jaw.

Alternatively the transducer 20 may be mounted on the jaw 14 at an opening 40 that is separate from anchor opening 19, as depicted in FIG. 5. Although not shown in FIG. 5, the transducer 20 may be coupled to the jaw 14 with a coupling material, and further secured with a tensioning spring or wedge in order to provide an additional securing mechanism for the transducer 20 to the jaw 14.

Figure 6:
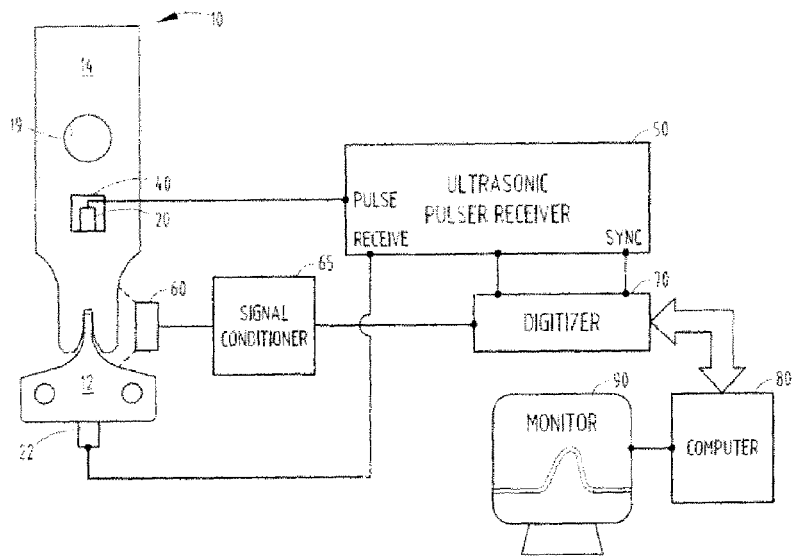
FIG. 6 is a schematic representation of a system or apparatus for nondestructive evaluation of the quality of a crimped wire connector during installation thereof.

FIG. 6 schematically illustrates a system or apparatus for nondestructive evaluation of the quality of a crimped wire connector in accordance with an embodiment of the invention. The system includes an ultrasonic pulser-receiver 50 for providing an electrical signal to transmitting ultrasonic transducer 20 that is converted into an ultrasonic wave, and for receiving an electrical signal from receiving transducer 22 indicative of a received waveform from receiving transducer 22. Although it is not required to analyze the quality of the crimp, alternatively a position sensor 60 may be included to detect the position of jaw 14 relative to anvil 12 and transmit an electrical signal via a signal conditioner 65 to a digitizer 70 that also receives signals from ultrasonic pulser-receiver 50. Positional and ultrasonic wave characteristic data can be measured, digitized and transmitted to a computer 80 during the crimping operation. This digitized information can be analyzed by a computer employing algorithms for comparing the measured information with similar information obtained previously for wire connectors having a known quality characteristic (e.g., characteristic of crimp quality, expected useful life, etc.). Analysis of the data may occur subsequent to the crimping process, however it is contemplated that real-time analysis of the data can occur during crimping to assess the quality of the crimp in real-time.

Figures 7A, 7B, 7C:
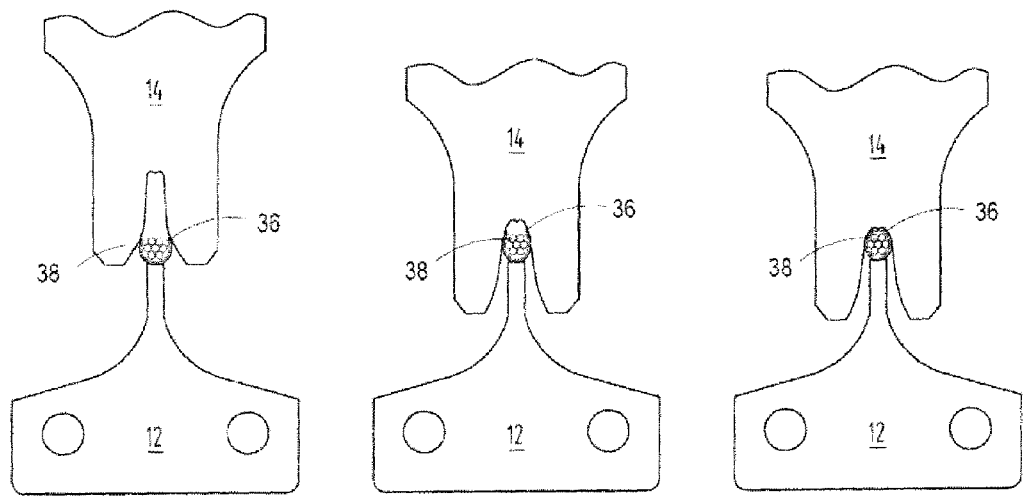
FIGS. 7a, 7b and 7c illustrate changes in the position of the jaw relative to the anvil, and changes in the shape of the terminal and wire at sequential times during closure of the tool and crimping of the terminal against the wire.

FIGS. 7a, 7b and 7c show the sequence of compression stages from the beginning to the end of the compression cycle and the changes in the shape of a terminal 36 and a wire 38 at sequential times during closure of the tool and crimping of the terminal 36 against the wire 38. The data that is collected from ultrasonic waves transversing the device according to the present invention begins prior to the initial compression stage, throughout each compression stage, and after the terminal is crimped.

As the ultrasonic waves are traversing the crimp tool and the jaw-anvil separation is decreasing, ultrasonic data and positional data may be detected and recorded. The sequence for measurement is as follows: (1) a synchronizing pulse begins the process by causing the jaw opening to be measured and by causing the ultrasonic pulser-receiver 50 to begin sending pulses to the ultrasonic transmitter 20, and starting the timing measurement for the digitizer (triggers the digitizer). The time (x-axis) and the received waveform from transducer 22 as ultrasonic amplitude (y-axis) are plotted on the monitor. A record of time, received waveform and jaw opening is made. This sequence is repeated every pulse cycle. A window may be set to record the first received waveform at the receiving transducer for every pulse cycle. The ultrasonic data and jaw position data can be recorded at a set rate (e.g., one pulse every two milliseconds). Typically, the transit time for the first received ultrasonic waveform is on the order of ten microseconds. Therefore the transit time is less than $1/100$ of the pulse cycle time. Consequently, first-received waveforms are plotted sequentially. Throughout the operation, the voltage pulses applied to the transmitting transducer remains uniform (i.e., each pulse applied to the transmit transducer is identical in shape and height).

Figure 8:
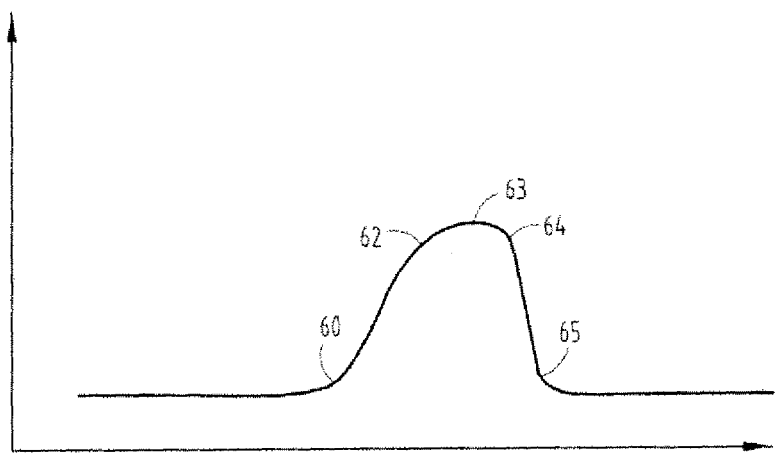
FIG. 8 illustrates a schematic diagram of a plot of the envelope of the Hilbert transform of the ultrasonic wave amplitude (y-axis) versus time (x-axis) that is characteristic of the crimping process.

FIG. 8 shows a schematic diagram of a plot of the envelope of the Hilbert transform of the ultrasonic wave amplitude (y-axis) versus time (x-axis) that is characteristic of the crimping process. During the crimping process, the amplitude of the ultrasonic wave propagated through the terminal-wire from the jaw to the anvil slowly begins to increase at a point of initial contact 60. As the compression cycle progresses, a point at 62 is reached at which the onset of maximum pressure occurs. Maximum ultrasonic transmission (amplitude) reaches a maximum at point 63. At point 64, maximum pressure is released, and separation between the jaw and the crimped connection occurs at point 65.

Figure 9:
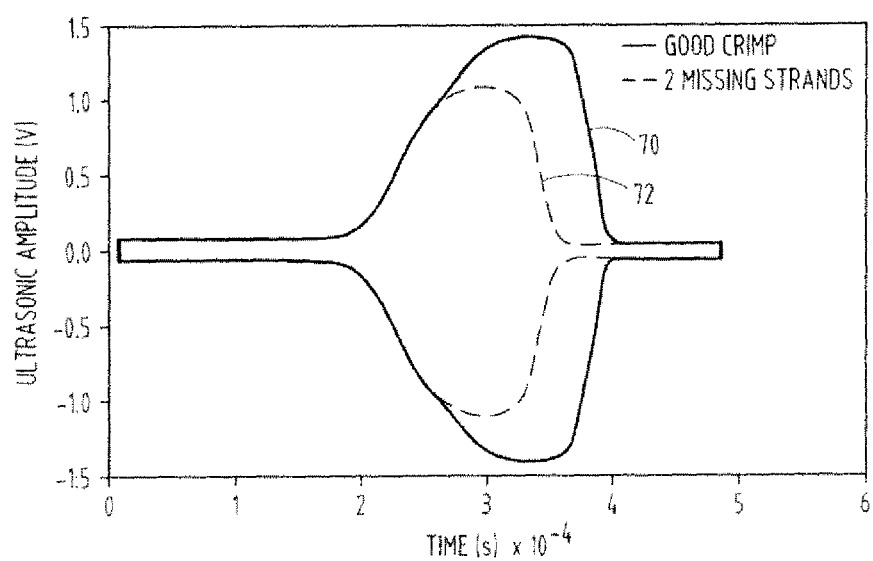
FIG. 9 illustrates a schematic diagram of a plot of the envelope of the received ultrasonic signals versus time for two crimped connections employing the same wire gauge and using the same tools and terminal, with curve 70 being for a good crimp, and curve 72 being for a crimp having two missing strands out of seven total strands.

FIG. 9 shows a schematic diagram of a plot of the envelope of the received ultrasonic signals versus time for two crimped connections employing the same wire gauge and using the same tools and terminal, with curve 70 being for a good crimp, and curve 72 being for a crimp having two missing strands out of seven total strands.

After collection of the raw data of ultrasonic wave amplitude versus time, the data may be analyzed in various ways in order to determine whether a quality crimp connection has resulted from the crimping process. A Hilbert Transform may be performed on the data to allow an energy-based analysis. Alternatively, a Fourier or other transform may be performed on the data to allow a frequency-based analysis.

Figure 10:
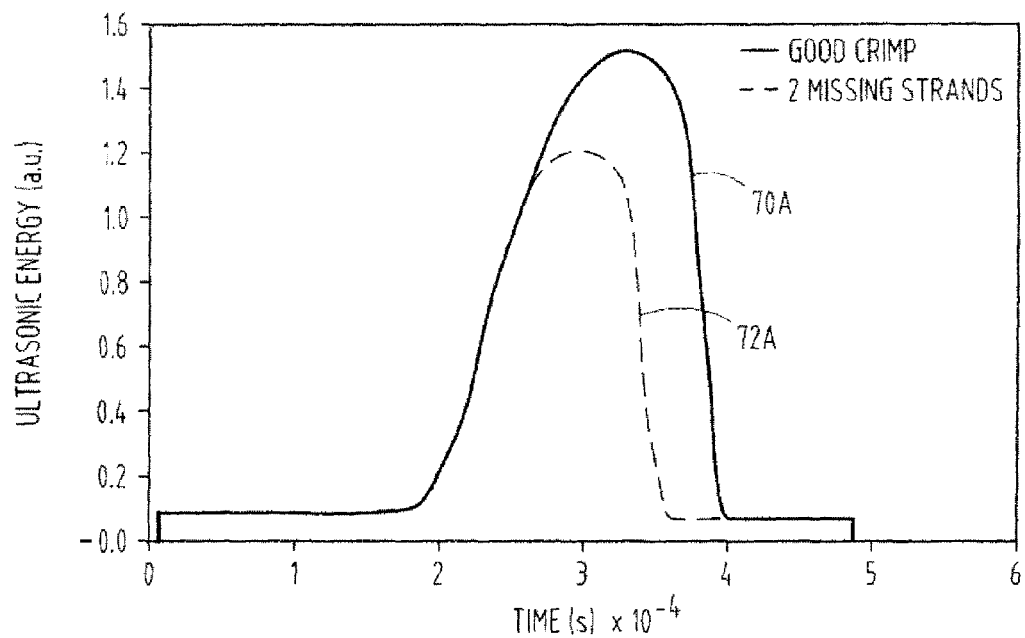
FIG. 10 is a plot of the amplitudes taken by Hilbert Transforms of the ultrasonic transmission responses shown in FIG. 9.
Figure 11:
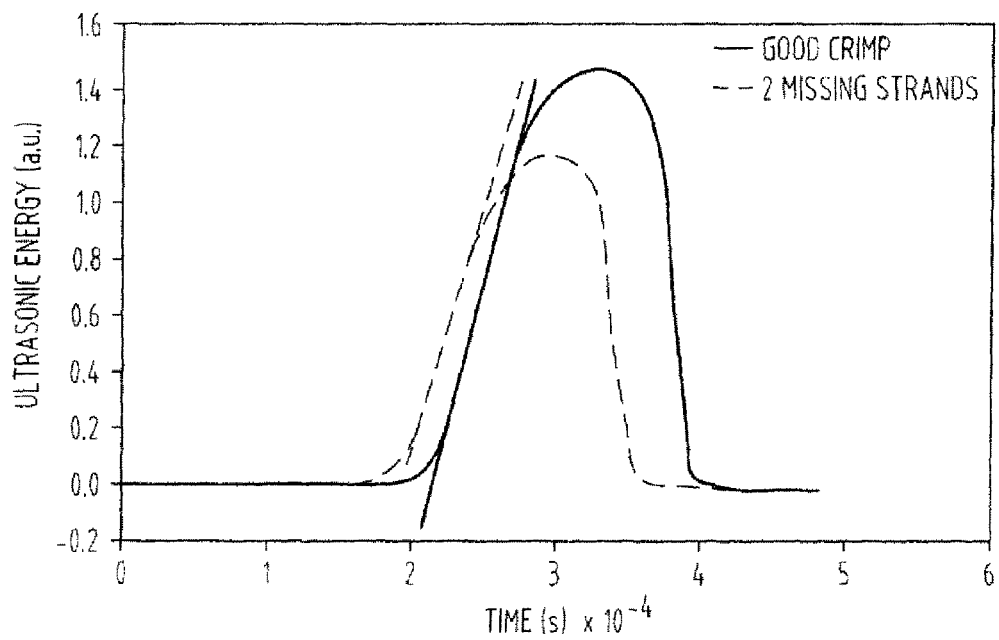
FIG. 11 illustrates that the slope between initial contact and onset of maximum pressure (plastic deformation) differs substantially for the good crimp as compared with the crimp missing two strands.

As shown in FIG. 10, data is shown after a Hilbert Transformation and a peak envelope detection algorithm has been applied to the raw data. Curve 70A represents the envelope of the Hilbert Transform of curve 70 shown in FIG. 9 and curve 72A represents the envelope of the Hilbert Transform of curve 72 shown in FIG. 9. The plotted data in FIGS. 9 and 10 show that a good crimp has a quantitatively different slope between the initial contact point and the onset of maximum pressure (plastic and elastic deformation) than the slope between initial contact and onset of maximum pressure for a bad crimp (e.g., a crimp having missing strands). Additionally, it can be observed that the maximum ultrasonic transmission energy achieved during the crimping process is greater for the good crimp than for the bad crimp.

Figure 12:
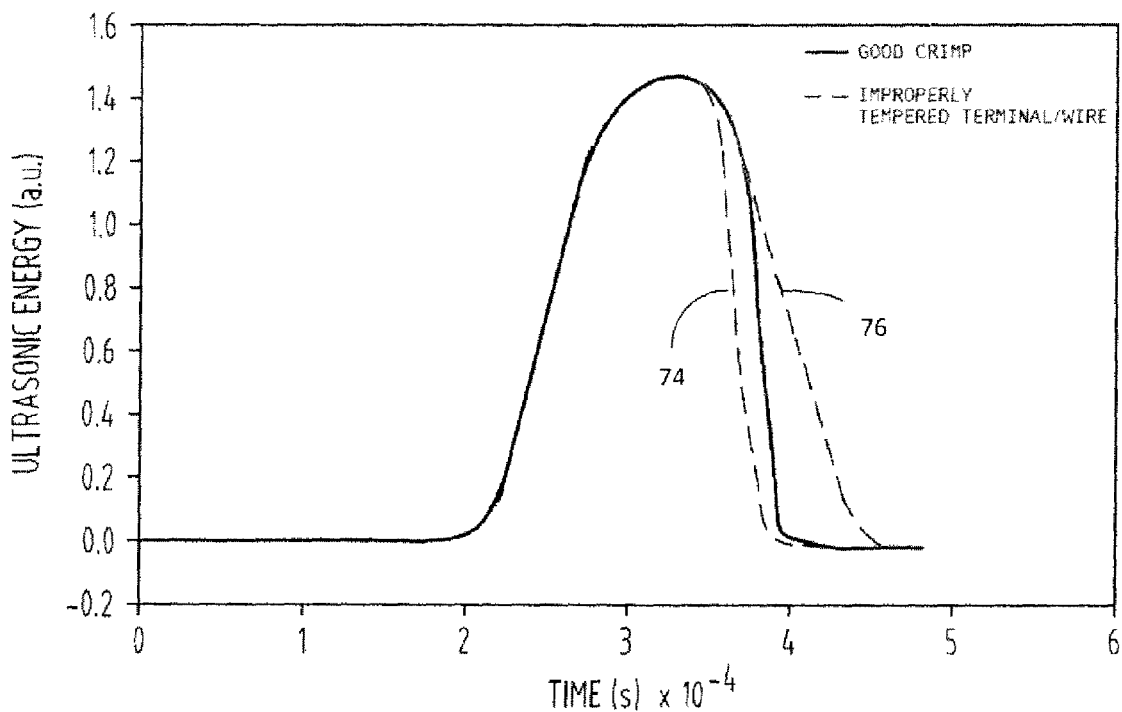
FIG. 12 illustrates that the slope between the maximum pressure release and the separation (elastic spring-back) is a measure of the ability for the crimped wire-terminal structure to maintain its conformality or elasticity.
Figure 13:
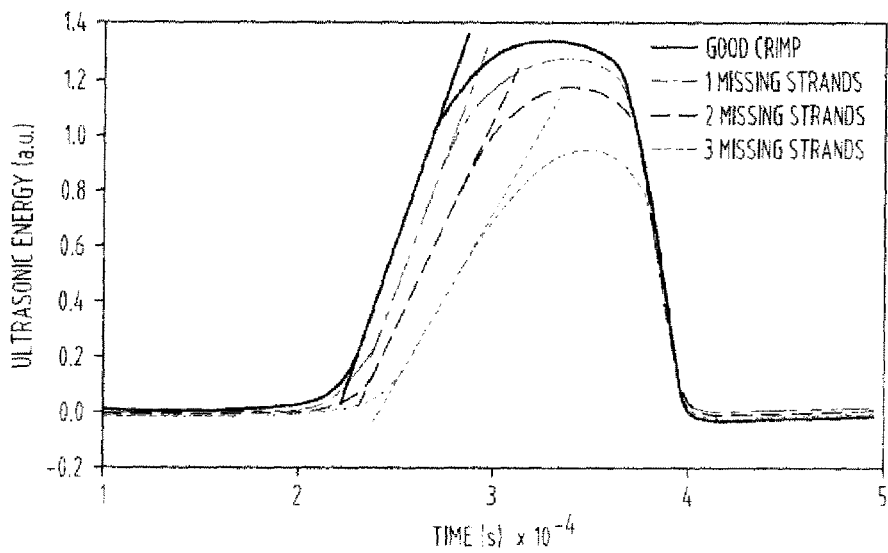
FIG. 13 illustrates that the slope between initial contact and onset of maximum pressure (plastic deformation) continually decreases with an increasing number of missing strands.

Also, the slope between the maximum pressure release and the separation (elastic spring-back) is a measure of the ability for the crimped wire-terminal structure to maintain its conformality or elasticity. This property depends upon the elastic properties of the wall of the terminal and the wire. If the temper of either the terminal or the wire is out of specification (as can sometimes occur when proper manufacturing procedures are not followed) then the slope will change. As shown in FIG. 12, the data analysis can also show an improperly tempered terminal or wire at the slope between the maximum pressure release and the separation. Curve 74 represents a wire/terminal with too much tempering and curve 76 represents a wire/terminal with not enough tempering to serve for a quality crimp.

Determination of numerical values is based on a number of cycles with good crimps. The mechanical performance of the machine can be verified by manufacturer's recommended procedures to meet or exceed specifications. The good crimps can be independently verified by destructive test procedures consistent with good practices. Once verified, the mean and standard deviation of the compression and pressure release slopes for the good crimp is determined and stored. Similarly, the maximum height can also be determined and stored. These values can subsequently be compared with each crimp formed during the full production cycle. Any crimp falling outside of a predetermined limit (e.g., more than three standard deviations above or below) can be rejected to assure that potential production problems are avoided.

The test interpretations can be based on the development of pathology maps, as demonstrated within the examples (e.g., missing strands). It is expected that the compression slope, the ultrasonic maximum transmission, and the pressure release or elastic spring-back slope can characterize the crimp quality. Other pathologies that can potentially be characterized include machine malfunctions, deviations from nominal design values for dimension or temper for the wire and/or terminal, the wire thickness, the presence of missing strands, wire contamination with foreign substances, insulation slivers or sections caught inside the crimp zone, etc. In one embodiment of the present invention, the apparatus may include a notification system which informs the user of the type of pathology detected in the crimp after the data has been analyzed.

For each pathology listed, a certain pattern among the slopes and the maximum pulse height will develop and hence identify the presence of a pathology.

Although the invention is expected to be particularly well suited for high speed automated crimping processes, the technology can be employed with manual (hand) operated crimping tools. The invention can also be employed on battery powered, electric or pneumatically powered hand tools. The mode of power or portability of the tooling is independent of the applicability of the technology. The same technology outlined above can be employed with tools of multiple jaws or anvils. It is not restricted to tooling with one jaw and anvil but can be applied to multi-pin indenter type tools. The technology disclosed herein can be incorporated into the design of new tools or it can be designed to form an add-on attachment that is field-installable.

Typical electronic and ultrasonic specifications for the components are as follows: transducers (typically damped units of diameter $1/4$ inches to $1/8$ inches) about 5 MHz to about 70 MHz, or from about 20 MHz to about 50 MHz, depending on wire gauge; pulser-receiver (analog from 1 MHz to 200 MHz bandwidth, with pulse width, pulse maximum voltage and pulse energy settings appropriate for transducer selection) with stable pulse rate settings. Digitizer minimum of 8 bits or better at 400 M sample/second digitizing rate or better, input levels to match output from pulser-receiver and input to match output from position sensor and signal conditioner. Position sensor sensitivity to 10 micrometer sensitivity and capacity to span full range of jaw-anvil motion.

The maintenance, reliability and safety factors largely depend upon the manufacturer's product to which the technology of this invention is implemented.

By combining ultrasonic date with positional information (jaw-to-anvil distance) substantially more physical information about crimp quality, including plastic deformation and elastic spring-back can be characterized. The additional information makes it more likely to identify crimps with limited service life due to contamination and improperly tempered terminals or connectors. The systems of this invention can be self calibrating. However, calibration can drift and should be repeated periodically. The period for recalibration can be determined by experience with the technology. Other than misalignment of transducers or jaw-anvil misalignment, sources of error are primarily improper adjustment or electronic settings, calibration drift of transducers and/or circuits, couplant/bond degradation between the transducer and bolt (e.g. FIG. 2), and couplant/bond degradation between the jaw/anvil and transducers (e.g. FIGS. 2 and 5). Analysis of the data collected shows good sensitivity to missing strand pathologies. Other pathologies and their signatures can be developed using the apparatus and processes described herein.

While preferred embodiments and example configurations of the invention have been herein illustrated, shown and described, it is to be appreciated that various changes, rearrangements and modifications may be made therein, without departing from the scope of the invention as defined by the appended claims. It is intended that the specific embodiments and configurations disclosed are illustrative of the preferred and best modes for practicing the invention, and should not be interpreted as limitations on the scope of the invention as defined by the appended claims and it is to be appreciated that various changes, rearrangements and modifications may be made therein, without departing from the scope of the invention as defined by the appended claims.

The invention claimed is:

1. A process for nondestructive evaluation of the quality of a crimped wire connector, comprising:
   providing a crimping tool having an anvil on which a wire circumscribed by a terminal is positioned, an upper jaw movable relative to the anvil to compress the terminal between the anvil and the jaw, a transmitting ultrasonic transducer mounted on one of the anvil and the jaw, and a receiving ultrasonic transducer mounted on the other of the anvil and jaw;
   moving the jaw relative to the anvil to close the distance between the jaw and the anvil, and thereby compress and crimp the terminal against the wire;
   transmitting ultrasonic waves from the transmitting ultrasonic transducer while moving the jaw relative to the anvil, such that the ultrasonic waves are propagated through the terminal and wire;
   receiving ultrasonic waves at the receiving transducer while moving the jaw relative to the anvil, wherein the ultrasonic wave comprises a voltage as a function of time;
   detecting and recording the voltage as a function of time that is received at the receiving ultrasonic transducer as the jaw is moving relative to the anvil;
   determining a rate of change of the detected and recorded voltage corresponding to at least one of compression and pressure release; and
   determining whether a pathology exists in the crimped wire connector by comparing the rate of change to a predetermined limit.

2. The process of claim 1, further comprising:
   detecting and recording the position of the jaw relative to the anvil as a function of time as the jaw is moved relative to the anvil.

3. The process of claim 2, wherein the transmitting ultrasonic transducer, the anvil, and the receiving ultrasonic transducer are axially aligned transverse to a length direction of the wire.

4. The process of claim 3, wherein the recorded voltage as a function of time is digitized and stored for subsequent evaluation by an algorithm operating on a computer.

5. The process of claim 4, wherein the algorithm comprises an energy based analysis algorithm.

6. The process of claim 4, wherein the algorithm comprises a frequency based analysis algorithm.

7. The process of claim 2, wherein the position of the jaw relative to the anvil and recorded voltage as a function of time are continuously sampled, detected and recorded from at least initial mutual contact between the terminal-wire arrangement and the jaw, and between the terminal-wire arrangement and the anvil, to a time at which separation between the jaw and the crimped connection occurs.

8. The process of claim 1, wherein the transmitted ultrasonic wave has a frequency in the range from about 5 MHz to about 70 MHz.

9. The process of claim 8, wherein the transmitted ultrasonic wave has a frequency in the range from about 20 MHz to about 50 MHz.

10. The process of claim 1, wherein the pathology comprises a pathology with wire tempering, terminal tempering, machine malfunction, wire thickness, missing wire strands, wire contamination with a foreign substance, or presence of an insulation section caught within the crimped connection.

* * * * *